United States Patent
Rieser et al.

(10) Patent No.: US 6,242,247 B1
(45) Date of Patent: Jun. 5, 2001

(54) METHOD FOR MAKING CARTILAGE AND IMPLANTS

(75) Inventors: Franz Rieser; Werner Muller, both of Wiesendangen; Pedro Bittmann, Zurich; Pierre Mainil-Varlet, Bern; Christoph P. Saager, Frieswil, all of (CH)

(73) Assignee: Sulzer Orthopedics Ltd., Winterthur (CH)

(*) Notice: Subject to any disclaimer, the term of this patent is extended or adjusted under 35 U.S.C. 154(b) by 0 days.

(21) Appl. No.: 09/194,867
(22) PCT Filed: Jun. 2, 1997
(86) PCT No.: PCT/CH97/00220
§ 371 Date: Dec. 4, 1998
§ 102(e) Date: Dec. 4, 1998
(87) PCT Pub. No.: WO97/46665
PCT Pub. Date: Dec. 11, 1997

(30) Foreign Application Priority Data
Jun. 4, 1996 (CH) .................................................. 1408/96

(51) Int. Cl.$^7$ .................................................. C12M 3/06
(52) U.S. Cl. .................................. 435/297.1; 435/297.5; 435/182; 435/382; 623/23.63
(58) Field of Search ............................. 435/1.1, 1.2, 372, 435/373, 382, 401, 297.1, 297.2, 297.5, 182; 623/9–11, 13, 16, 18, 11.11, 13.11, 13.17, 13.18, 16.11, 23.63; 424/422, 424, 425, 428, 93.1, 93.7

(56) References Cited

U.S. PATENT DOCUMENTS 4,308,351 * 12/1981 Leighton et al. .
4,559,299 * 12/1985 Rotman .
4,904,259 * 2/1990 Itay .

(List continued on next page.)

FOREIGN PATENT DOCUMENTS

| 4306661 | 9/1994 | (DE) . |
| 63-196281 | * 8/1988 | (JP) . |
| 9012603 | 11/1990 | (WO) . |
| 9319168 | 9/1993 | (WO) . |

OTHER PUBLICATIONS

Biomaterials 10, Mar. 1996 "Encapsulation of Artificial Tissues in Polyelectrolyte Complexes" pp. 1049–1051.
Biomaterials 6, Mar. 1994 "Engineering of Cartillage Tissue Using Bioresorable Polymer Carriers in Perfusion Culture" pp. 451–456.

(List continued on next page.)

Primary Examiner—William H. Beisner
(74) Attorney, Agent, or Firm—Birch, Stewart, Kolasch & Birch, LLP (57) ABSTRACT

Cartilage tissue and implants comprising cartilage tissue are produced in vitro starting from cells having the ability to form an extracellular cartilage matrix. Such cells are brought into a cell space (1) and are left in this cell space for producing an extracellular cartilage matrix. The cells are brought into the cell space to have a cell density of ca. $5 \times 10^7$ to $10^9$ cells per cm$^3$ of cell space. The cell space (1) is at least partly separated from a culture medium space (2) surrounding the cell space by a semi-permeable wall (3) or by an open-pore wall acting as convection barrier. The open-pore wall can be designed as a plate (7) made of a bone substitute material and constituting the bottom of the cell space (1). The cells settle on such a plate (7) and the cartilage tissue growing in the cell space (1) grows into pores or surface roughness of the plate, whereby an implant forms which consists of a bone substitute plate (7) and a cartilage layer covering the plate and whereby the two implant parts are connected to each other in positively engaged manner by being grown together.

20 Claims, 10 Drawing Sheets

U.S. PATENT DOCUMENTS

| | | | |
|---|---|---|---|
| 5,053,050 | * | 10/1991 | Itay . |
| 5,272,083 | * | 12/1993 | Butz et al. . |
| 5,306,311 | * | 4/1994 | Stone et al. . |
| 5,326,357 | * | 7/1994 | Kandel . |
| 5,656,492 | * | 8/1997 | Glowacki et al. . |
| 5,723,331 | * | 3/1998 | Tubo et al. . |
| 5,726,060 | * | 3/1998 | Bridges . |
| 5,759,851 | * | 6/1998 | Mathus . |
| 5,891,455 | * | 4/1999 | Sittinger et al. . |
| 5,904,716 | * | 5/1999 | Gendler . |

OTHER PUBLICATIONS

Clinical Orthopaedics and Related Research, Jun. 1984 "Chondrocytes Embedded in Collagen Gels Maintain Cartilage Phenotype During Long–Term Cultures" pp. 231–239.

Biomaterials 1, Jan. 1989 "Gorwth of Osteoblasts on Porous Calcium Phosphate Ceramic: An In Vitro Model for Biocompatiligty Study" pp. 63–67.

* cited by examiner

FIG. 11 bar ≅ 10μm

FIG. 12

FIG. 13 bar = 2μm

METHOD FOR MAKING CARTILAGE AND IMPLANTS

This application is the national phase under 35 U.S.C. §371 of prior PCT International Application No. PCT/CH97/00220 which has an International filing date of Jun. 2, 1997 which designated the United States of America.

The invention is in the field of medicinal engineering and concerns a method according to the generic part of the first independent claim, i.e. a method for producing cartilage tissue and implants for the repair of enchondral and osteochondral defects. Furthermore, the invention concerns an arrangement for carrying out the method and implants produced according to the method.

Cartilage tissue substantially consists of chondrocytes and extracellular matrix. The extracellular matrix mainly consists of collagen type II and proteoglycanes the components of which are exuded into the intercellular space where they are assembled to form macro molecules. The chondrocytes make up about 5% of the volume of the cartilage tissue of a grown-up individual.

Articular cartilage coating the ends of flexibly joined bones takes over the function of the load distribution in the loaded joint. For this function the cartilage tissue is capable to take up water and to release it again under pressure. Furthermore, the cartilage surfaces serve as sliding surfaces in the joints.

Cartilage is not vascularized and therefore its ability to regenerate is very poor, in particular in grown-up individuals and if the piece of cartilage to be regenerated exceeds but a small volume. However, articular cartilage often shows degenerations due to wear or age or injuries due to accidents with a far larger volume than might be naturally regenerated. This kind of defect of the cartilage layer makes movement and strain of the affected joint painful and can lead to further complications such as e.g. inflammation caused by synovial liquid which comes into contact with the bone tissue due to the defect in the cartilage layer covering the bone.

For these reasons efforts have been made for quite some time to replace or repair missing or damaged cartilage, especially articular cartilage by corresponding surgery.

It is known to repair defects concerning articular cartilage or articular cartilage and the bone tissue beneath it by milling the defect location to form a bore of an as precise geometry as possible, by extracting a column of cartilage and bone of the same geometry from a less strained location of e.g. the same joint by means of boring or punching and by inserting this column into the bore. In the same manner, larger defects with several bores are repaired (mosaic plasty). These methods are successful but the actual problem is substantially shifted from a strained part of a joint to a less strained part of the joint and therefore, is not really solved.

It is also suggested, e.g. in the publication U.S. Pat. No. 3703575 (Thiele), to repair defects of cartilage with purely artificial implants (e.g. gels containing proteins and polysaccharides). It shows, however, that only restricted success can such be achieved and therefore in recent development solutions to the problem have been thought in various directions, in particular based on vital autologous or homologue cells. Vital chondrocytes or cells able to take over a chondrocyte function are e.g. cultivated in vitro and then implanted; or vital chondrocytes are introduced in artificial implants; or vital cartilage tissue is cultivated at least partly in vitro and is then implanted. This means that in these recent developments the aim is to produce vital cartilage in vitro and to implant such cartilage or to populate a defect site with cartilage forming cells which cells are then to build tissue at least similar to cartilage.

Examples of such methods are described in the following publications:

According to the method described in U.S. Pat. No. 4,846,835 (Grande), chondrocytes taken from the patient are multiplied in a mono-layer culture and, for further reproduction, are then introduced into a three-dimensional collagen matrix in form of a gel or a sponge in which matrix they settle and become immobile. After ca. three weeks of cell reproduction, the defect cartilage location is filled with the material consisting of the collagen matrix and the cells. In order to hold the implant in the defect location, a piece of periosteum is sutured over it. The cartilage regeneration in the region of this kind of transplant is considerably better than without the transplant.

According to the method described in U.S. Pat. No. 5,053,050 (Itay), chondrocytes or cells able to take over a chondrocyte function are introduced into a bio-compatible, resorbable matrix ($32 \times 10^6$ to $120 \times 10^6$ cells per $cm^3$) in which matrix the cells are immobilized. This matrix is implanted, whereby a cartilage-like tissue forms in vivo. The chondrocytes used for the implant are previously cultivated, first in a mono-layer culture and then suspended, whereby they assemble to form aggregates of 30 to 60 cells.

According to the method described in U.S. Pat. No. 4,963,489 (Naughton), again a three-dimensional, artifical matrix is used as carrier material for the implant. This matrix is used for the cell culture preceding the implantation and is covered with a layer of connective tissue for better adhesion and better supply of the cells to be cultivated. After in vitro cell reproduction on the three-dimensional matrix, the matrix is implanted. The implanted cells form the cartilage tissue in vivo.

According to the method described in PCT-WO90/12603 (Vacanti et al.), again a three-dimensional matrix is used which matrix consists of degradable polymer fiber materials and on which matrix the cells settle. The cells cultivated on the matrix or in monolayer cell cultures and then introduced into the matrix are implanted adhering to the matrix and therefore, in an immobilized state. The matrix is degraded in vivo and is gradually replaced by extracellular matrix built by the cells.

According to the method described in U.S. Pat. No. 5,326,357 (Kandel), chondrocytes are applied to a layer of filter material (MILLICELL®-CM having a pore size of 0.4 μm) in a mono-layer with a cell density of $1.5 \times 10^6$ cells per $cm^2$. In vitro culturing of the monolayer produces a thin cartilage layer in two to four weeks which, in its structure obviously corresponds to the natural articular cartilage and can be implanted as such.

It is also known that cartilage can be cultivated in so called high density cell cultures. Cells are applied to a carrier and are cultured in a higher density than used for mono-layer culturing. The culture medium is added only one to two hours after bringing the cells onto the carrier. After one to three culture days, the cell layer on the carrier contracts and so-called microspheres with diameters in the range of 1 mm form. On further culturing, a cartilage-like tissue forms inside these microspheres while fibrous cartilage (perichondrium) forms on their surface. For implants, this kind of inhomogeneous tissue is not suitable.

Sittinger et al. (Biomaterials Vol. 17, No. 10, May 1996, Guilford GB) suggest to introduce vital cells into a three-dimensional matrix for growing cartilage in vitro and to then enclose the loaded matrix into a semi-permeable membrane. During the cartilage growth, this membrane is to prevent the culture medium to wash away compounds produced by the cells and being used for constructing the extracellular matrix. Implantation of cell cultures enclosed in this kind of membranes is also known for preventing immune reactions.

All methods named above attempt to produce cartilage at least partly in vitro, i.e. to produce cartilage using vital natural cells under artificial conditions. The problem encountered in these attempts is the fact that chondrocytes in these in vitro conditions have the tendency to de-differentiate into fibroblasts relatively rapidly, or the fact that it is possible to differentiate fibroblasts to a chondrocyte function under very specific culture conditions only. By the de-differentiation the chondrocytes among other things loose the ability to produce type II collagen which is one of the most important compounds of cartilage tissue. According to the methods mentioned above, the problem of de-differentiation of chondrocytes is solved by immobilizing the chondrocytes in correspondingly dense cultures in a monolayer or in a three-dimensional matrix. It shows that in this manner chondrocytes reproduce themselves without substantial de-differentiation and form an extracellular matrix which is at least similar to the extracellular matrix of natural cartilage. The three-dimensional matrix is mostly not only used for immobilizing the cells but also for mechanical stability after implantation which is needed because none of the cartilage tissues produced in the named manner has a stability which could withstand even a greatly reduced strain.

The object of the invention is to create a device with which suitable cartilage tissue or implants which at least partly consist of such cartilage tissue can be produced in vitro, the cartilage or implant serving for implantation, especially implantation in articular cartilage defects. For achieving this object it is necessary to create an in vitro environment, in particular a three-dimensional such environment, in which environment chondrocytes or other cells capable of a chondrocyte function do not de-differentiate over a longer culture period and perform their function actively or in which environment cells differentiate to become active chondrocytes respectively. By solving the problem of this environment, the main part of the object is achieved as not de-differentiating, vital chondrocytes according to their natural function produce the extracellular matrix characteristic for cartilage and together with this form the cartilage tissue to be created.

The implants produced according to the invention consist at least partly of cartilage tissue produced in vitro and are especially suited for the repair of enchondral or osteochondral joint defects. They are to be producible for any possible depth of such a defect and a defect repaired with the inventive implant is to be able to carry a normal load as soon as possible after implantation, i.e. a load created either by pressing or by shearing forces.

This object is achieved by the method as defined in the claims.

The inventive method is based on the finding that chondrocytes can build satisfactory cartilage tissue if it is made possible that a sufficiently high concentration of compounds produced by the cells and segregated into extracellular spaces is achieved in a short initial phase and is maintained during the whole culture period. Under these conditions the differentiated function of the chondrocytes is fully maintained (they do not de-differentiate into fibroblasts) and/or it is possible to differentiate corresponding cells, especially mesenchymal stem cells or other mesenchymal cells or even fibro-blasts to a corresponding function.

The first condition is fulfilled by creating a cell community in which there is, at least at the beginning of the culture period, a density of cells such that the cells are capable to produce the amount of compounds necessary for the mentioned concentrations in the spaces between the cells. The second condition is fulfilled by accommodating the cell community in a restricted cell space in which washing out of the named compounds from the extracellular spaces is prevented.

The named compounds are especially autocrine factors and substances serving as components for building the extracellular structure. These components are especially aggrecanes, link-proteins and hyalorunates for building proteo-glycane-aggregates and preliminary stages of collagens to eventually form collagen-fibrils of type II.

According to the inventive method, the cells are not immobilized for the in vitro culture but have space at their disposition, space without a three dimensional, artificial matrix in which space the two conditions mentioned above are fulfilled, in which space it is however largely left to the cells how they are to settle relative to each other. It shows that in this kind of free cell space, cells fully practice their chondrocyte-function and a cartilage tissue having sufficient stability for implantation and being able to carry at least part of the normal load after implantation can be cultured.

According to the inventive method, cells which are capable of a chondrocyte-function are introduced into an empty cell space, i.e. into a space containing culture medium only, such that there is a cell density of ca. $5 \times 10^7$ to $10^9$ cells per cm$^3$ in the cell space. This density amounts to a space occupation of ca. 5% to 100% at an approximate cell volume of $10^3$ $\mu m^3$.

The cell space has at least partly permeable walls and is introduced into a space filled with culture medium for the length of the culture period which medium is periodically renewed in known manner. During the culture period, the cell space is arranged to be stationary in the culture medium or it is moved in it (relative movement between cell space and culture medium surrounding the cell space).

The permeability of the permeable parts of the cell space wall and the relative movement are to be matched to the relative dimension of the cell space (depending on the cartilage to be produced) such that the condition of the washing-out-prevention is fulfilled.

For all cases, semi-permeable wall regions (semi-permeable membranes) with a permeability of 10.000 to 100.000 Dalton (10 to 100 kDa) are suitable, especially for agitated cultures and for cell spaces of large dimensions (three-dimensional forms). The named autocrine factors and components for building the macromolecules of the extracellular cartilage matrix have molecular weights which are such that they cannot pass through a membrane with the named permeability.

It shows that for stationary cultures and cell spaces with at least one small dimension (thin layers) open-pore walls with considerably larger pores (up to the region of 10 to 20 $\mu$m) which cannot be effective as semi-permeable walls but merely as convection barriers are sufficient and that possibly the cell space can even be open on one side.

Especially in cell spaces not being moved and containing cells at a density in the lower region of the given density range, the cells settle in the direction of gravity and form cartilage tissues in the form of layers. For producing more three-dimensional cartilage forms, agitated cell spaces prove to be advantageous.

For specific cultures and especially for specific forms and sizes of cell spaces the optimal arrangement (with or without movement of the cell space in the culture medium) and the optimal condition of the wall of the cell space or the permeable parts of this wall respectively must be determined by experiment.

The cell space has substantially three functions:

The cell space keeps the community of the (not immobilized) cells together at a sufficient density such that they do not loose their specific functionality;

the cell space restricts the growth of cartilage such that by choice of the form of the cell space the form of the cartilage being formed is controlled;

the cell space wall allows the supply of the cells with culture medium but prevents the washing out of the substances produced by the cells and necessary for the growth of cartilage.

For producing implants which only partly consist of cartilage tissue, a part of the permeable wall of the cell space can additionally have the function of an implant part as will be described in more detail further below.

The cells to be brought into the cell space are chondrocytes, mesenchymal stem cells or other mesenchymal cells. These cell types are isolated in known manner from cartilage tissue, from bone or bone marrow or from connective tissue or fatty tissue. Fibroblasts are also suited, e.g. if factors are added to the culture medium or the cell space which factors effect differentiation of the fibroblasts to chondrocytes or if the cells are treated with this kind of factor before they are brought into the cell space. The cells can also be multiplied in vitro before being brought into the cell space.

It is not necessary to isolate specific cell types from donor tissue, i.e. mixtures of different cells as usually contained in such tissues can be brought into the cell space as such. It also shows that a complete separation of the cells from the intracellular matrix of the donor tissue is not necessary and thus possibly tissue particles or mixtures of isolated cells and tissue particles can be brought into the cell space instead of cells only. However, care has to be taken that the necessary cell density is achieved in the cell space possibly by partly separating the cells from their extracellular matrix, e.g. by means of a short enzymatic digestion.

It shows that with the known culture media such as e.g. HAM-F12 to which 5 to 15% serum is advantageously added, good results can be achieved. Furthermore, known growth factors and other components of culture media which support the reproduction of the cells and the forming of the cartilage matrix can be added to the culture medium.

It shows that in the culture conditions created according to the inventive method the chondrocytes remain active and do not de-differentiate such that the space is filled with cartilage tissue in a culture period in the range of ca. three weeks. The cartilage tissue being formed can, as soon as it has a sufficient mechanical strength, be removed from the cell space and e.g. be further cultivated floating freely in the culture medium or it can remain in the cell space up to directly before being used.

Cartilage tissue produced according to the inventive method is used as implant as implant part or when containing autologous cells as cell-auto-transplant or it can be used for scientific in vitro purposes.

The following Figures illustrate the inventive method, the arrangement for carrying out the inventive method as well as examples of implants produced by means of the inventive method. The shown examples are implants for repair of enchondral and osteochondral defects in joints. However, using the inventive method it is also possible to produce other implants such as e.g. auditory bones or cartilage for plastic surgery e.g. nose cartilage, orbital floors, ear conchs or parts thereof.

Figure 1:
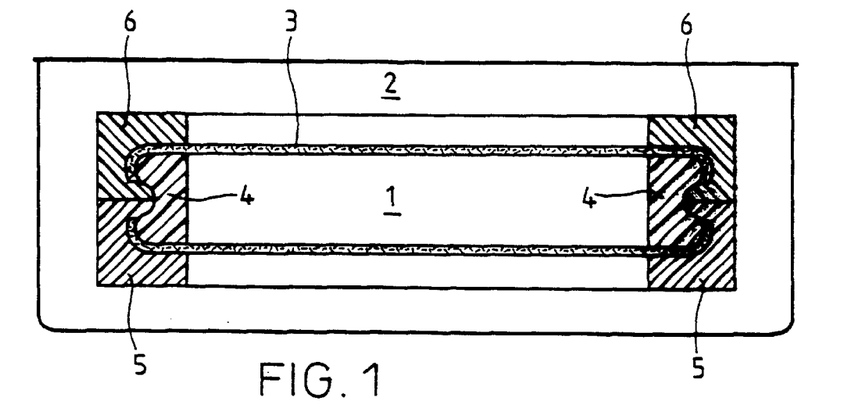
FIGS. 1 to 4 show four exemplified arrangements (in section) for carrying out the inventive method for in vitro production of cartilage tissue.

FIG. 1 shows in section an exemplified arrangement for the inventive in vitro production of cartilage tissue. This arrangement substantially consists of a defined cell space 1 into which the cells are introduced and which is arranged in a culture medium space 2. At least part of the boundary between the cell space 1 and the culture medium space 2 is formed by a permeable wall, e.g. a semi-permeable membrane 3. The remaining parts of the boundary separating the cell space 1 from the culture medium space 2 are not permeable and consist e.g. of plastic components which give the cell space 1 the predetermined form and hold the semi-permeable membrane in place.

In the shown example, an inner ring 4 and two outer snap-rings 5 and 6 together with two e.g. substantially circular pieces of semi-permeable membrane enclose a cell space 1 in the form of a circular disc.

The semi-permeable membrane 3 has a permeability of 10.000 to 100.000 Dalton. It e.g. consists of the same material as a corresponding dialyse tube.

It is obvious that in the same manner as shown in FIG. 1, cell spaces of the most various forms can be created, into which spaces cells are introduced and in which spaces these cells build cartilage tissue, the cartilage tissue substantially assuming the form of the cell space 1 or the form of the one part of cell space 1 which during the culture period faces downward in the direction of gravity.

The culture medium space 2 is a freely selectable space in which the culture medium is periodically exchanged in known manner. If the cell space 1 is to be moved in the culture medium space 2 the culture medium space is e.g. a spinner bottle.

Using an arrangement according to FIG. 1, the inventive method is e.g. carried out as follows:

Cells, tissue particles or mixtures of cells and/or tissue particles as described further above are suspended e.g. in culture medium and are introduced into the free cell space such that the cell density is in the range between $5 \times 10^7$ and $10^9$ cells per $cm^3$.

The cell space is closed and introduced into the culture medium space and is left there for a period of time in the range of approximately three weeks.

The cartilage tissue formed in the cell space is removed from the cell space and is either cultivated further swimming freely on a culture medium or is directly used as implant or as transplant or for scientific investigations respectively.

In the a cell space according to FIG. 1, implants consisting of cartilage tissue, e.g. auditory bones, nose cartilage, orbital floors or parts thereof are produced.

Figure 2:
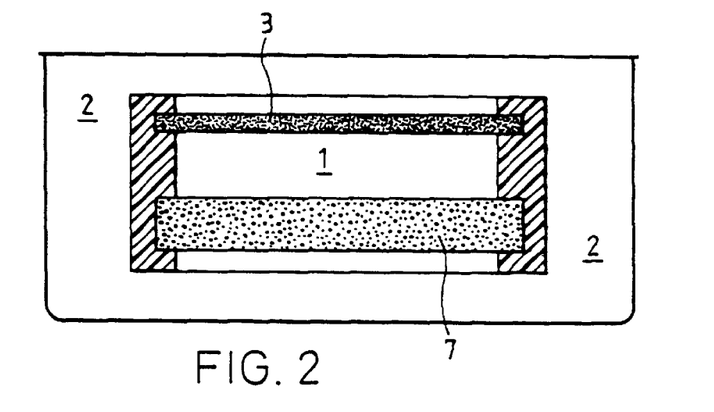

FIG. 2 shows a further embodiment of a cell space for carrying out the inventive method. The cell space 1 is flat and its one side is limited by an open pore, rigid or plastically deformable plate 7 made of a possibly biologically degradable bone substitute material, the other side by a permeable wall, e.g. a semi-permeable membrane 3 or a more coarsely porous wall. The cell space has a height of e.g. ca. 3 to 5 mm and any flat form and extension.

A cell space as shown in FIG. 2 is especially suited for the production of an implant for repair of a osteochondral defect. The implant comprises not only the cartilage tissue grown in the flat cell space but also the bone substitute plate 7. This bone substitute plate 7 thus has substantially two functions: during the growth of the cartilage, it serves as permeable wall for the cell space 1 and in the finished implant, it serves as anchoring substrate for the cartilage layer, whereby after implantation this bone substitute material is colonized in known manner by cells immigrating from the adjacent vital bone tissue.

In order for the bone substitute plate 7 to be able to fulfill the second function named above care must be taken that by a corresponding arrangement of the cell space in the culture medium space the cells settle over the whole inner surface of the bone substitute plate 7 at least for a case in which the initial cell density is such that the cells have a settling tendency. Therefore, the cell space 1 is e.g., as shown in FIG. 2, arranged to be stationary with the bone substitute plate 7 facing downward such that the cells settle on the bone substitute plate 7 due to the effect of gravity.

Furthermore, the bone substitute plate 7 must be formed such that the cartilage tissue growing in the cell space 1 is able to grow together with the bone substitute plate 7 in an intermediate region, thus forming a two part implant which can resist shearing forces. This kind of growing together is achieved by choosing the porosity of at least the one surface of the bone substitute plate on which the cartilage is cultivated such that the collagen fibrils built in the extracellular cartilage matrix can grow into the pores and can such anchor the new cartilage in the bone substitute plate. It shows that for this kind of anchoring of the collagen fibers, pores of ca. 1 to 20 μm are suitable.

Furthermore, it is advantageous if a part of the cells which are brought onto the surface of the bone substitute plate for cultivating the cartilage settle in uneven places or in pores such that the growing cartilage tissue growth is connected to the bone substitute material in these uneven places and pores in a kind of positive engagement. It shows that cells easily settle in uneven places or pores if these have a size of at least 20 μm, ideally between 20 and 50 μ.

Therefore, the bone substitute plate 7 is to fulfill the following conditions:
 In order for the cells to be able to be nourished from the culture medium through the bone substitute plate it must comprise pores which form continuous canals (open porosity).
 in order for the bone substitute plate to serve at least as a convection barrier against the washing away of larger molecules the pores must not be too large and the thickness of the plate must not be too small.
 In order for the collagen fibrils being built in the growing cartilage tissue to be anchored in the pores of the plate the pores must not be larger than 20 μm.

In order for the cells to be able to settle in uneven places or pores in the surface of the bone substitute plate such uneven places or surface pores (surface roughness) having sizes of at least ca. 20 μm must be provided at least on the one part of the surface facing the growing cartilage layer.

It shows that with bone substitute plates having a correspondingly rough surface, having an open porosity with pore sizes in the range of 2 to 20 μm and having a thickness of 0,5 to 3 mm, advantageously 0,5 to 1,5 mm satisfactory results can be achieved. With a plate thickness larger than ca 0,5 to 1 mm, the region facing away from the bone substitute plate can also have a coarser porosity, e.g. pores with sizes up to 300 to 700 μm such as known from bone substitute materials. This kind of porosity favors the in vivo vascularization of the bone substitute material.

As bone substitute material, known osteo-inductive and/or osteo-conductive materials are suitable, advantageously biologically degradable such materials which have the mentioned open porosity and which can be processed to rigid or plastically deformable plates. Plastically deformable plates can e.g. be produced from collagen I, from collagen II and hydroxyapatite or from poly-lactic acid. Rigid plates can be formed from tricalcium-phosphate, from hydroxyapatite or from other inorganic bone substitute materials.

Treatment of the bone substitute plate 7 with an attachment factor is unnecessary.

In a cell space according to FIG. 2 comprising a correspondingly open-pored bone substitute plate 7, not only cartilage tissue is grown in vitro but also an implant is produced which comprises a pre-formed, grown together cartilage/bone-intermediate region.

Figure 3:
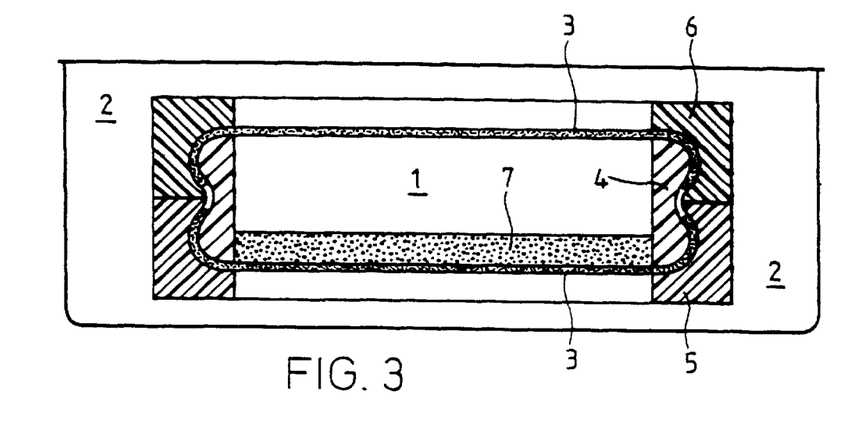

FIG. 3 shows a further, exemplified arrangement for carrying out the inventive method. In principle this is a combination of the methods as carried out in arrangements according to FIGS. 1 and 2. The bone substitute plate 7 is not arranged as part of the permeable wall of the cell space 1 but lies within the cell space which cell space is e.g. limited by semi-permeable membranes 3. It is obvious that in this kind of arrangement the bone substitute plate 7 does not have to take over the function of a convection barrier and that due to this the porosity and thickness of the plate can be chosen at greater liberty.

The arrangement shown in FIG. 3 is especially suitable for thin, plastically deformable bone substitute plates 7 which are complicated to handle as cell space walls.

Figure 4:
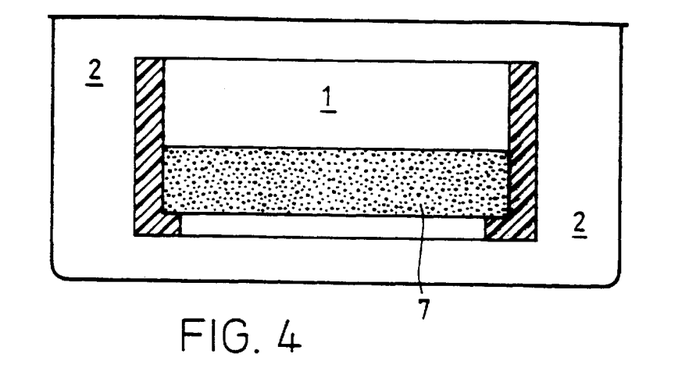

FIG. 4 shows schematically a further embodiment of a cell space 1 which space is especially suitable for cultivating very thin cartilage layers which are grown together with a bone substitute plate. In opposition to the cell space according to FIGS. 1 to 3, the cell space in FIG. 4 is open towards the top such that at least in the fist one to two weeks cultivation must take place under stationary culture conditions. In opposition to similar, known arrangements (e.g. U.S. Pat. No. 5,326,357, Kandel) a bone substitute plate 7 is provided as carrier for the cells and the cells are not applied to the carrier as monolayer and are not immobilized with the help of an attachment factor.

Figure 5:
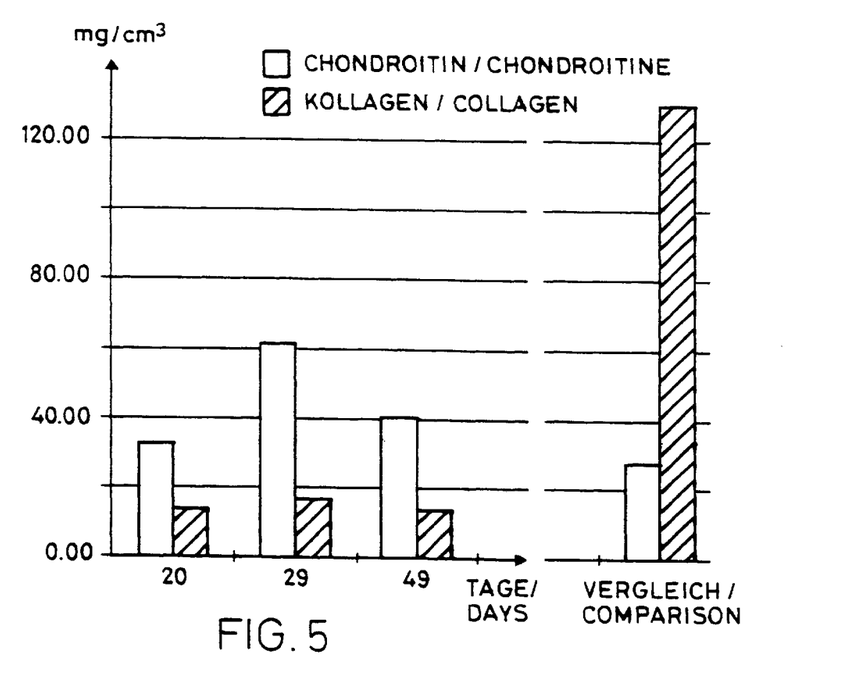
FIGS. 5 to 7 show chondroitin and collagen contents of different experimental cartilage cultures (of cultures according to the inventive method and of reference cultures according to known methods) in comparison with natural articular cartilage.
Figure 6:
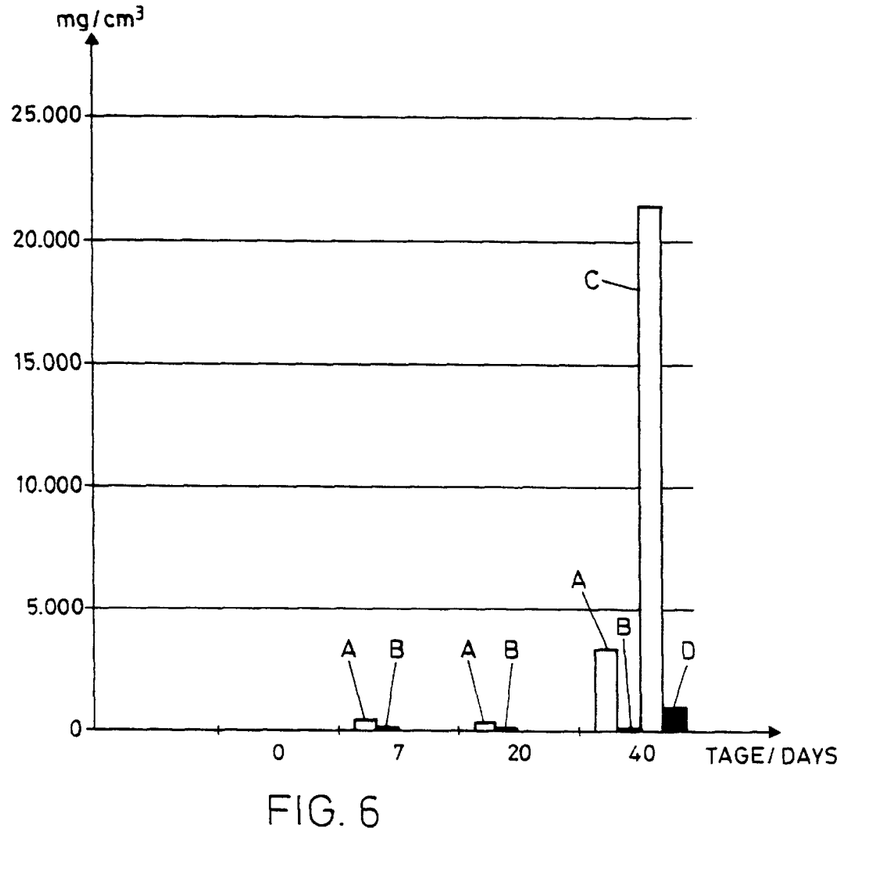
Figure 7:
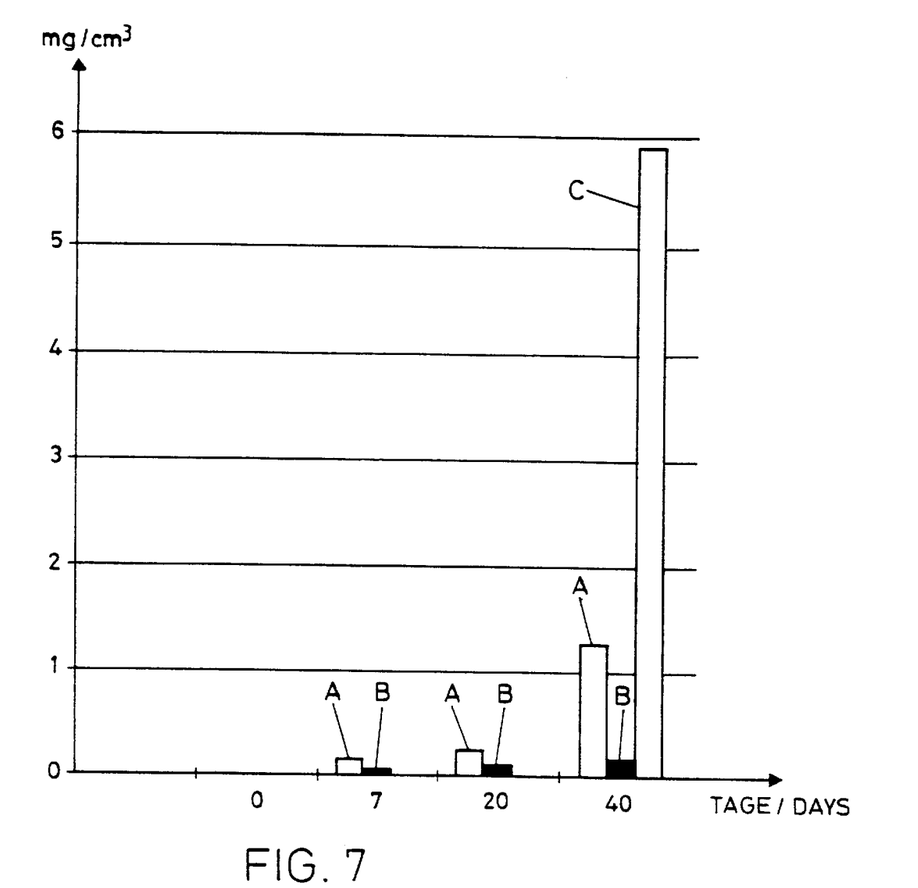

FIGS. 5 to 7 show results from experiments with the inventive method (experimental arrangement substantially as outlined in FIG. 1). Dialyse tubes were used as semi-permeable membranes.

Chondrocytes were isolated from bovine shoulders using known isolation methods. The cells were introduced into the dialyse tubes and these were moved in a spinner bottle during the culture period, whereby the cells settled on the bottommost end of the tubes. HAM-F12 with 5 to 15% serum was used as culture medium. The culture medium was changed every two days.

FIG. 5 shows the contents of chondroitin sulfate and collagen of the cartilage tissue produced according to the inventive method (in μg per ml of cartilage tissue) as a function of the duration of the culture period (20, 29 and 49 days) in comparison with corresponding values of cartilage from bovine shoulders (age: eighteen months). The results show that the content of chondroitin sulfate can be even higher in the cartilage produced in vitro than in natural cartilage, that the content of collagen however is considerably lower.

FIGS. 6 and 7 also show, as a function of the duration of the culture period (0, 7, 20 and 40 days), chondroitin sulfate (FIG. 6) and collagen contents (FIG. 7) in reference cultures A and B and of cartilage tissue grown according to the inventive method after 40 days of culture time (C: cartilage growing in the cell space in the region of the settled cells, D: culture medium in the cell space above the settled cells). For references, chondrocytes were embedded in alginate spheres and cultivated in a stationary culture (reference A) and in a spinner bottle (reference B).

FIGS. 6 and 7 make it clear that the cartilage structure in the experimental arrangement according to the invention is considerably more successful than in the reference experiments.

Figure 8:
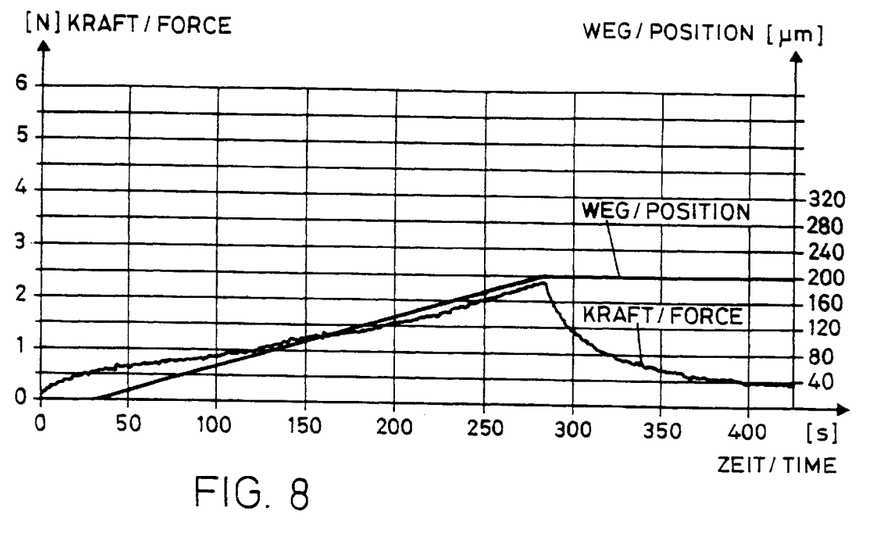
FIGS. 8 and 9, for illustrating the mechanical properties of cartilage produced according to the inventive method, show forces straining such cartilage (FIG. 8) and straining native cartilage (FIG. 9)
Figure 9:
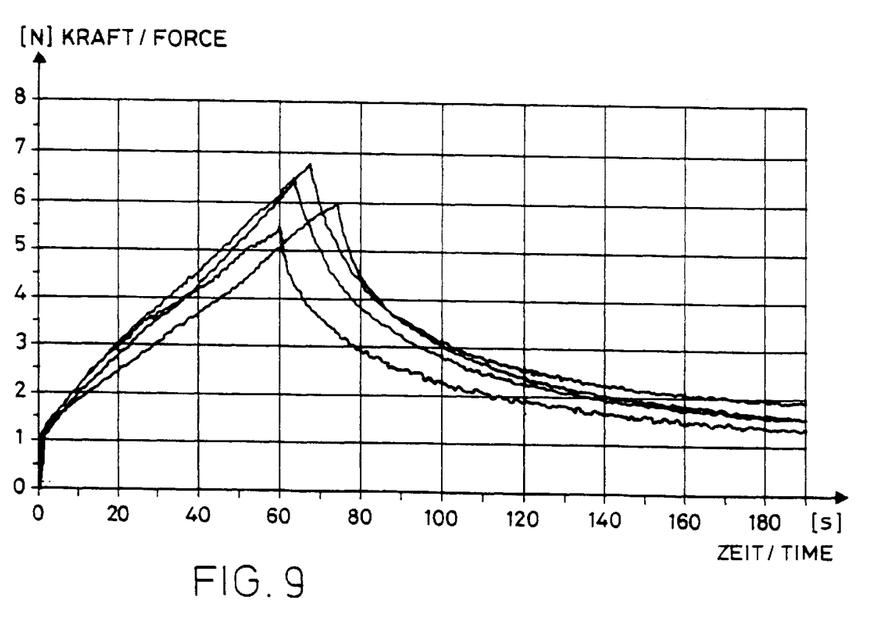

FIGS. 8 and 9 show results of stress experiments on cartilage produced according to the invention (FIG. 8) and on native cartilage (FIG. 9) in order to illustrate the mechanical properties of the cartilage produced according to the inventive method (for culture conditions see above) compared with the mechanical properties of native bovine cartilage. The experiment consists in pressing a punch into the cartilage with a constant speed (1 micrometer per second) and to stop the punch at a penetration depth of 200 μm while registering the punch force. This force first rises approximately proportionally to the penetration depth and after stopping the punch decreases (visco-elastic force reduction due to loss of liquid of the cartilage tissue).

The two FIGS. 8 and 9 show the punch force in Newton (N) as a function of he time in seconds (s). In FIG. 8 the registering of the depth of penetration (travel) is shown in μm.

The stress experiment with the cartilage produced according to the invention (FIG. 8) was carried out with a punch having a diameter of 20 mm and shows a maximal pressure of ca. $0.8N/cm^2$. The experiment with the native cartilage was carried out with a punch having a diameter of 5 mm and shows a maximal pressure of ca. $30N/cm^2$.

Figure 12:
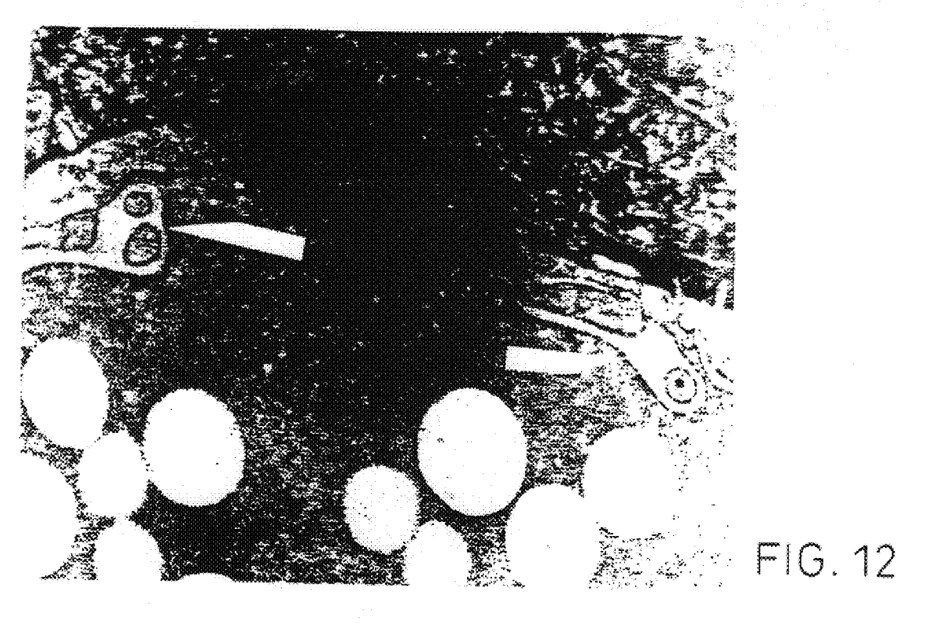
Figure 13:
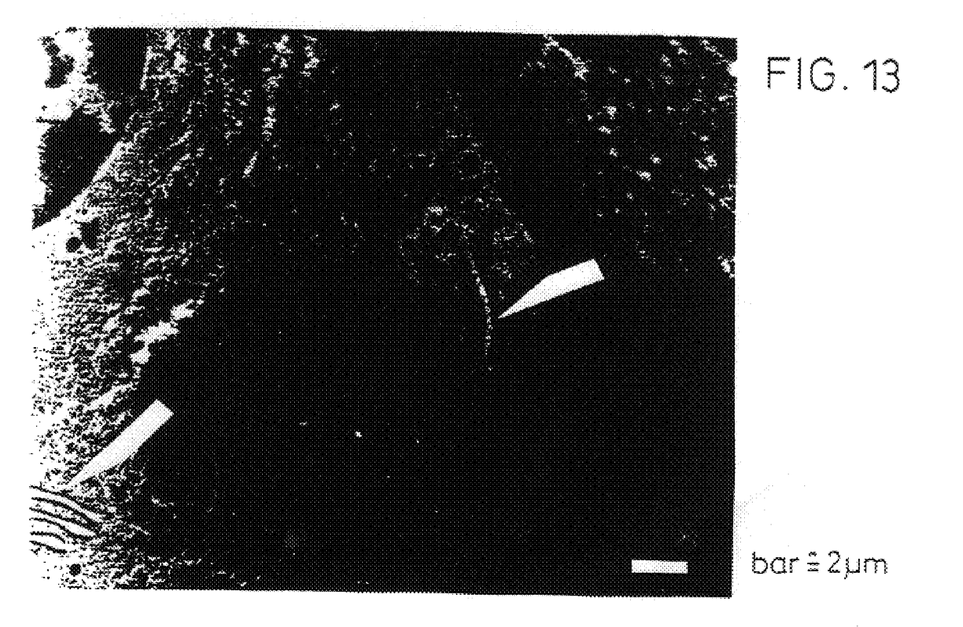

The considerably smaller maximal pressure of the cartilage produced according to the inventive method can be explained in connection with FIGS. 10 to 13. These Figures show light-microscopical micrographs (FIGS. 10 and 11) and electron-microscopical micrographs (FIGS. 12 and 13) of cartilage produced according to the inventive method (FIGS. 10 and 11) and of human cartilage from the medium zone (FIGS. 12 and 13).

Figure 10:
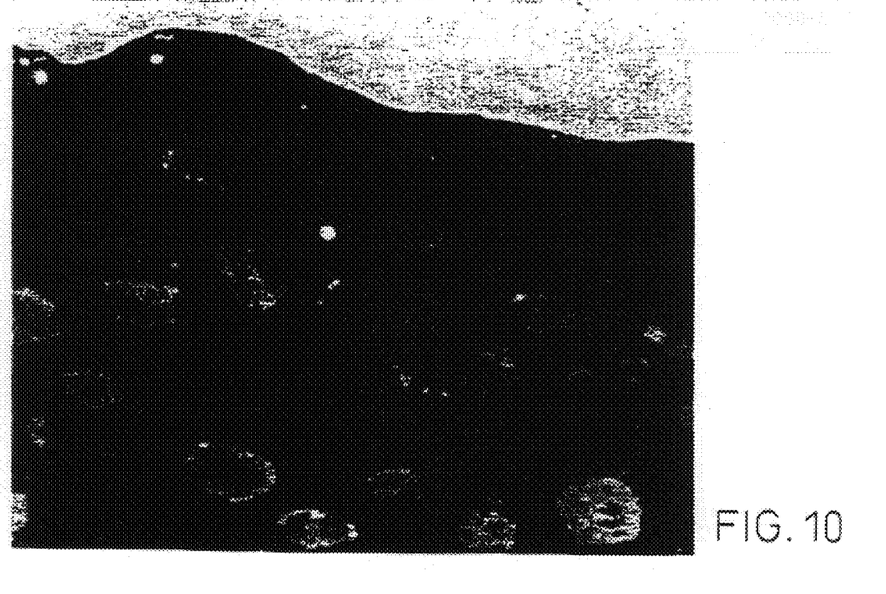
FIGS. 10 to 13 show light-microscopical and electron-microscopical micrographs of cartilage produced according to the inventive method and of native cartilage.
Figure 11:
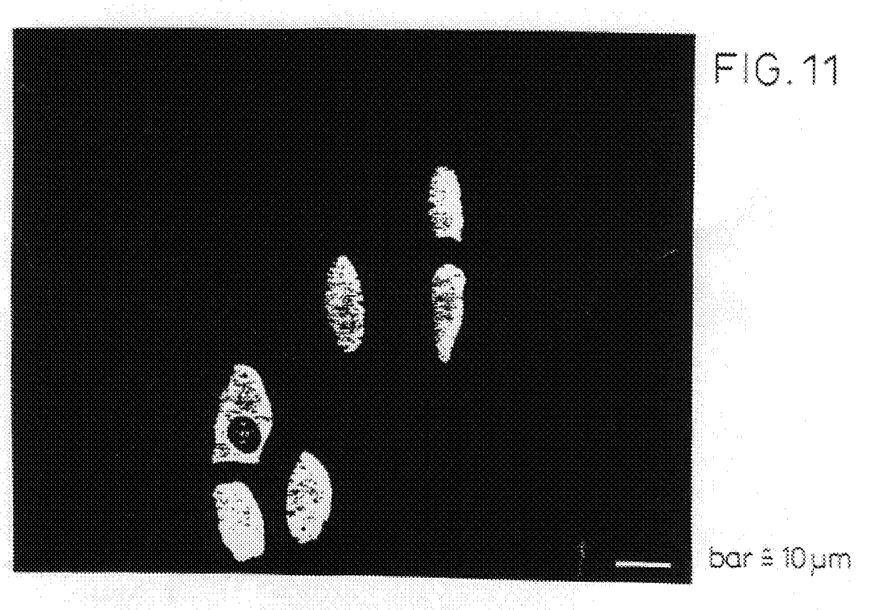

FIGS. 10 and 11 clearly show that the cartilage produced according to the inventive method contains considerably more chondrocytes than the native cartilage which can be interpreted as growth stage for the cartilage cultivated in vitro. The same interpretation is suggested by FIGS. 12 and 13 in which organelles are easily visible in the chondrocytes (marked with arrows). In the native cartilage, the organelles are narrow suggesting little synthesis activity; in the cartilage produced according to the invention they are distinctly enlarged which suggests an intense synthesis activity, i.e. a growth stage.

Further electron-microscopical investigations of inventively produced cartilage tissue show that the collagen fibrils form a dense net therein but that they are thinner than in native cartilage (after completed growth) and that they are arranged having random directions. Therefore, the cartilage tissue produced according to the invention must be looked at as a kind of embryonic cartilage tissue which, however has the ability to develop in vivo (after implantation) into [grown-up] cartilage.

Figure 14:
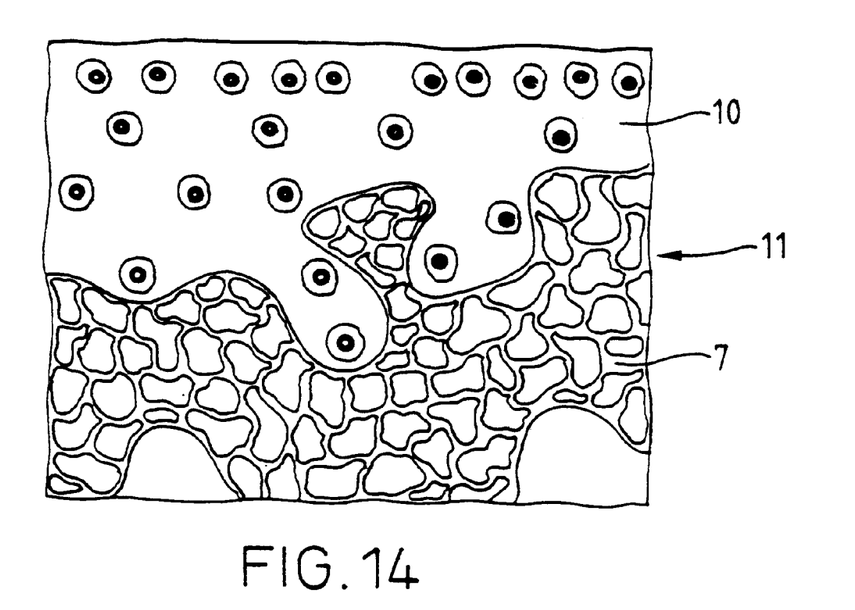
FIG. 14 shows a section through an implant produced according to the inventive method as illustrated in FIG. 2 or 3, the implant comprising a carrier layer and a cartilage layer (boundary region between the two layers in section perpendicular to the layers)

FIG. 14 schematically shows a histological section (magnification ca. 100-fold) through the intermediate region between cartilage tissue and bone substitute plate of an implant which was produced in an arrangement according to one of the FIGS. 2 to 4. The cartilage tissue 10 and the bone substitute plate 7 are connected to each other in an intermediate region in the manner of positive engaging means due to the cartilage tissue having grown into uneven surface places of the bone substitute plate 7.

Figure 15:
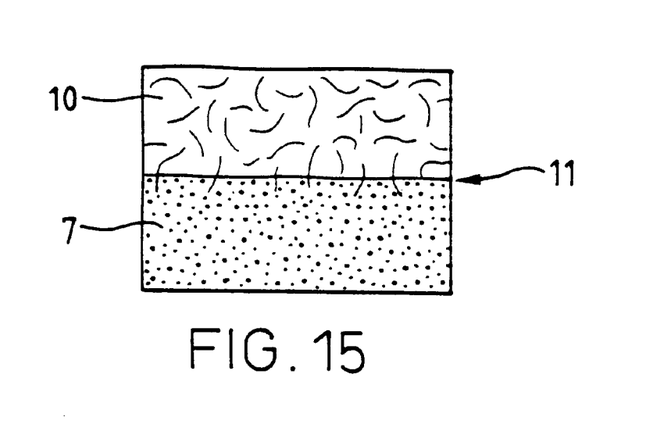
FIGS. 15 and 16 show exemplified embodiments of the inventive implants according to FIG. 14 in section perpendicular to the cartilage layer.
Figure 16:
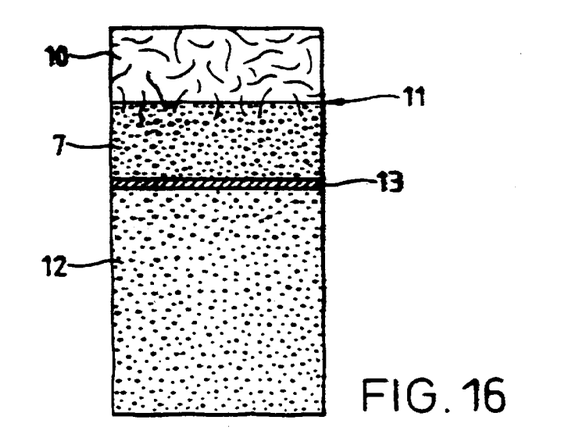

FIGS. 15 and 16 show exemplified embodiments of implants which are produced according to methods as described in connection with FIGS. 2 to 4 (section through cartilage layer 10). The implants comprise an intermediate region in which the cartilage tissue is grown together with the bone substitute plate 7, as shown in FIG. 14.

After a culture period of a few weeks, the bone substitute plate 7 with the cartilage layer 10 having grown on it is separated from the other wall components of the cell space. Before implantation, the implant consisting of the cartilage layer 10 and the bone substitute plate 7 is reduced to the demanded size and form, if required, and/or is fixed to a further piece 12 of bone substitute material.

For processing the implant taken from the cell space, common surgical methods are used, such as e.g. punching, laser cutting or milling. For enlarging the bone substitute plate, a further piece 12 of a similar or different bone substitute material is attached on the one side of the bone substitute plate 7 opposite to the cartilage layer 10, using a known advantageously biologically degradable cement.

After implantation, bone forming cells from the native environment migrate into the open-pore bone substitute material of the bone substitute plate 7 and of the attached piece 12 and micro-vessels grow into the pores of the material. As a result of this a natural bone tissue develops which gradually replaces the bone substitute material (7, 12, 13) being gradually degraded. Hereby it is to be expected that the cartilage cultivated in vitro is mineralized in the intermediate region 11.

FIGS. 17 to 20 show enchondral and osteochondral defects which are repaired with exemplified embodiments of inventive implants.

Figure 17:
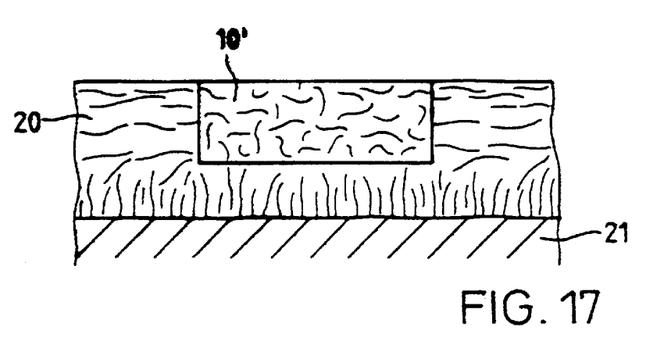
FIGS. 17 to 20 show examples of applications of implants produced according to the inventive method for the repair of enchondral and osteochondral joint defects (sections perpendicular to the cartilage layer).

FIG. 17 shows an enchondral defect with a defined form made by drilling or milling, i.e. a defect which lies in the native cartilage layer 20 and does not affect the bone tissue 21 underneath the cartilage layer 20. This kind of defect has, in the human case, a depth of maximally ca. 3 mm and can affect any extent of the cartilage surface. A piece of cartilage tissue 10' is inserted into the prepared defect which cartilage tissue was e.g. cultivated in an arrangement according to FIG. 1 and which cartilage tissue after cultivation was made to fit the form of the defect by cutting or punching, if required.

For a satisfactory fixation of the implant in the defect it is sufficient at least for small implants to slightly deform the implant elastically on implantation (press fit). With larger defects the implant is fixed with known means: e.g. with a piece of periosteum which is sutured or glued over the implant, with a glue being introduced between native cartilage and implant (e.g. fibrin glue) or by suturing the implant to the surrounding native cartilage.

Figure 18:
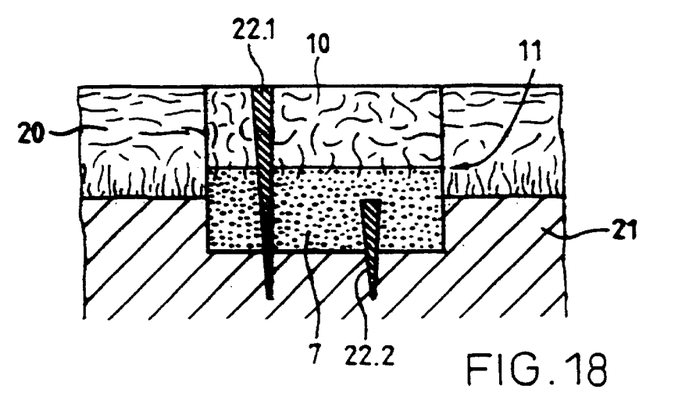

FIG. 18 shows a small osteochondral defect which has been prepared for implantation by drilling an opening having a defined form (surface extension up to ca. 10 mm, depth up to ca. 3 mm in the bone tissue), i.e. a defect which does not only affect the native cartilage tissue 20 but also the bone tissue 21 beneath it. This defect is repaired with an implant according to FIG. 15, which implant is fixed with one or several pins. Two pins are shown. The one pin 22.1 is driven through the implant from its surface by the surgeon, the other pin 22.2 is previously arranged in the bone substitute plate 7 of the implant and is driven into the bone by pressing on the surface of the implant.

Obviously, it is also possible to fix the implant in the defect according to FIG. 18 with other fixing means than pins.

From FIG. 18 it can be seen that in the repaired region the considerable shearing forces which act upon the intermediate region between bone 21 and cartilage 20 when straining the joint are taken over by the intermediate region 11 where the cartilage layer grown in vitro is grown together with the bone substitute plate 7.

Instead of an implant consisting of a cartilage layer 10 cultivated in vitro and a bone substitute plate 7, as shown in FIG. 18, the same defect can also be filled with a filling substance and further repaired with a piece of cartilage tissue cultivated in vitro (without bone substitute plate), in the same way as this is shown in FIG. 17. For taking up the shearing forces in such a case e.g. pins 22.1 reaching right through the implant are to be provided.

Figure 19:
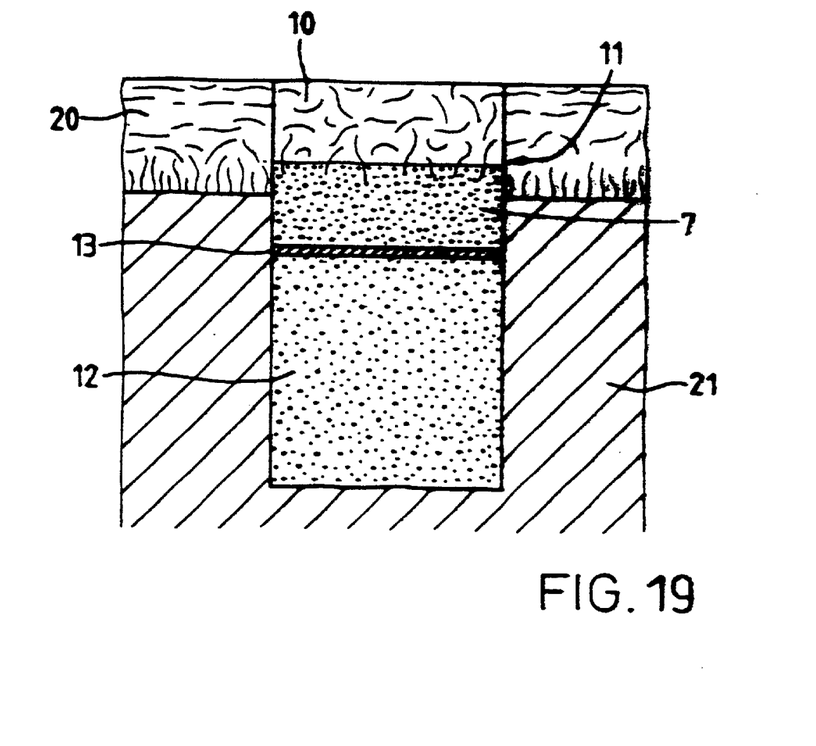

FIG. 19 shows a prepared osteochondral defect having a depth of 20 to 30 mm and repaired by implantation of an inventive implant according to FIG. 16. Shearing forces are again taken up by the region where the cartilage layer 10 and the bone substitute plate 7 are grown together. As the cement-connection 13 is positioned within the native bone 21 it is not strained by shearing and thus need not be reinforced by means of a pin.

The repair shown in FIG. 18 can also be carried out by filing the lower part of the bore with bone substitute material and by implanting an implant according to FIG. 15, possibly by means of a cement layer 13.

For larger osteochondral defects a plurality of implants according to FIG. 19 can be provided (mosaic plasty).

Figure 20:
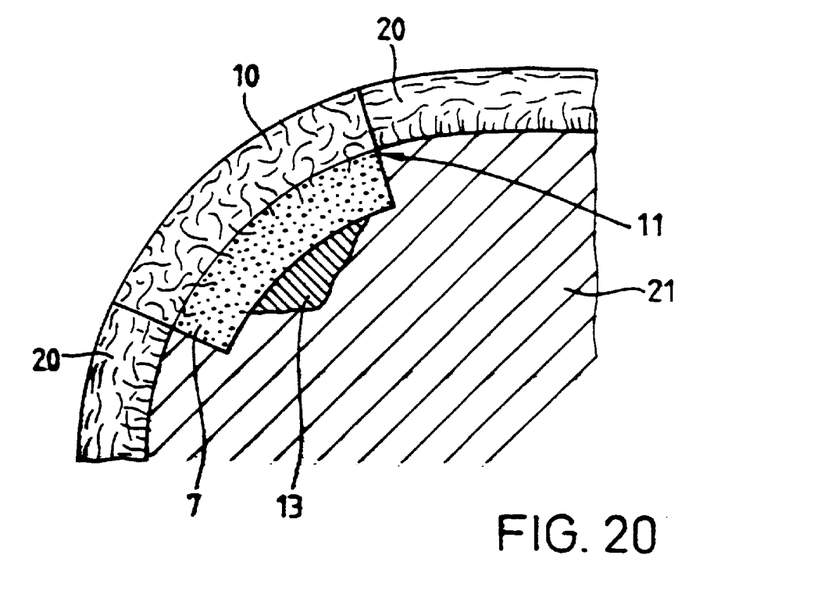

FIG. 20 shows a large and deep osteochondral defect. It is so large that the cartilage area to be repaired can no longer be approximated with an even area. This kind of defect can, as indicated further above, be repaired with mosaic plasty. However, as the inventive implants are not limited regarding surface size and as the bone substitute plates 7 can be made of a plastically deformable material, the defect is more easily repaired according to FIG. 20 with an implant according to FIG. 15. For this purpose, the defect is cut out to a depth of a few millimeters into bone 21 and to a defined form, deeper regions are filled with a plastic bone substitute material and the implant is positioned in the defect and fixed with suitable means.

What is claimed is:

1. A device for producing in vitro cartilage tissue and an implant comprising cartilage tissue, comprising:
   a cell space for receiving cells and culture medium and having a predefined form, said cell space being limited by cell space walls having an inside and an outside surface, wherein said cell space walls are at least in part semi-permeable or have an open porosity suitable as a convection barrier, and wherein the inside surface of said cell space walls does not discourage cell attachment; and
   a means for positioning said cell space in a culture medium such that at least the semi-permeable or porous part of the cell space walls are immersed in said culture medium, and wherein at least one of said cell space walls is a bone substitute plate having a porosity of 300 to 700 $\mu$m on a side facing away from the cell space.

2. The device according to claim 1, wherein the semi-permeable part of the cell space walls has a permeability of 10,000 to 100,000 Dalton.

3. The device according to claim 1, wherein the cell space walls have an open porosity of 1 to 20 $\mu$m and a thickness of 0.5 to 3 mm.

4. The device according to claim 3, wherein the open-pore layer is a bone substitute plate and wherein the cell space is arranged in such a manner that the bone substrate plate forms a bottom of the cell space.

5. The device according to claim 4, wherein the bone substitute plate is rigid.

6. The device according to claim 4, wherein the bone substitute plate is plastically deferrable.

7. The device according to claim 4, wherein the bone substitute plate is biologically degradable.

8. The device according to claim 4, wherein the bone substitute plate is not degradable.

9. The device according to claim 1, wherein the cell space has a flat form with two substantially parallel faces and that the two faces are formed by two of a semi-permeable membrane or by two of an open-pore layer.

10. A device for producing in vitro cartilage tissue and an implant comprising cartilage tissue, comprising:
    a cell space for receiving cells and culture medium and having a predefined form, said cell space being limited by cell space walls having an inside and an outside surface, wherein said cell space walls are at least in part semi-permeable or have an open porosity of 1 to 20 $\mu$m and a thickness of 0.5 to 3 mm and are suitable as a convection barrier, and wherein the inside surface of said cell space walls does not discourage cell attachment; and
    a means for positioning said cell space in a culture medium such that at least the semi-permeable or porous part of the cell space walls are immersed in said culture medium,
    wherein the open-pore layer is a bone substitute plate having a porosity of 300 to 700 $\mu$m on a side facing away from the cell space, and
    wherein the cell space is arranged in such a manner that the bone substrate plate forms a bottom of the cell space.

11. The device according to claim 10, wherein the bone substitute plate has a surface facing the inside of the cell space with a roughness of at least 20 $\mu$m.

12. The device according to claim 10, wherein the cell space further comprises a permeable wall outside of the bone substitute plate.

13. A method for producing in vitro cartilage tissue and an implant comprising cartilage tissue, comprising the steps of:
    (a) providing a cell space of a predefined form, said cell space being limited by cell space walls having an inside and an outside surface, wherein said cell space walls are at least in part semi-permeable or have an open porosity suitable as a convection barrier and wherein the inside surface of said cell space walls does not discourage cell attachment;
    (b) providing cells with a chondrogenic potential of $5\times10^7$ to $10^9$ per cm$^3$ of said cell space;

(c) introducing a mixture consisting of said cells and a suitable culturing medium, or consisting of tissue particles and a suitable culturing medium into said cell space so as to form a culture medium space;

(d) positioning said cell space in culturing medium, such that at least the semi-permeable or porous part of the cell space walls are immersed in said culturing medium;

(e) maintaining a suitable culturing condition for a time period of sufficient duration to allow said cartilage tissue and an implant comprising cartilage tissue to grow in said cell space.

14. The method according to claim 13, wherein said tissue particles comprise at least one of chondrocytes, mesenchymal stem cells, fibroblasts, or mixtures thereof.

15. Method according to claim 13, wherein the cells are chondrocytes, mesenchymal stem cells, fibroblasts or mixtures thereof.

16. Method according to claim 15, wherein the cells are multiplied in a cell culture before being introduced into the cell space.

17. Method according to claim 13, wherein the cell space is arranged to be stationary in the culture medium space or is moved in it during step (e), and that at least part of the cell space wall comprises a semi-permeable membrane with a permeability of 10,000 to 100,000 Dalton.

18. Method according to claim 17, wherein said cell space further comprises an open-pore, rigid or plastically deformable plate made of a bone substitute material.

19. Method according to claim 13, wherein the cell space is arranged to be stationary in the culture medium space during step (e) and that at least part of the cell space wall is designed as an open-pore layer with pores of a size of around 20 $\mu$m.

20. Method according to claim 19, wherein the open-pore layer is a plate made of a bone substitute material and that the cell space is arranged such that the plate is positioned such that the cells brought into the cell space settle on the plate.

* * * * *